(12) United States Patent
Choi et al.

(10) Patent No.: US 10,180,429 B2
(45) Date of Patent: Jan. 15, 2019

(54) MOLECULE IMMOBILIZATION PATTERNS AND METHOD FOR FORMING THE SAME

(71) Applicant: SMALL MACHINES CO., LTD., Daejeon (KR)

(72) Inventors: Jun Kyu Choi, Gumi-si (KR); Jung Hoon Lee, Seoul (KR); Seung Soo Han, Seoul (KR); Choo Yeon Kim, Seoul (KR); Na Hyun Song, Seoul (KR)

(73) Assignee: SMALL MACHINES CO., LTD., Daejeon (KR)

( * ) Notice: Subject to any disclaimer, the term of this patent is extended or adjusted under 35 U.S.C. 154(b) by 346 days.

(21) Appl. No.: 14/952,263

(22) Filed: Nov. 25, 2015

(65) Prior Publication Data

US 2017/0023564 A1    Jan. 26, 2017

(30) Foreign Application Priority Data

Jul. 22, 2015   (KR) ........................ 10-2015-0103881

(51) Int. Cl.
*G01N 33/543*   (2006.01)
*G01N 33/554*   (2006.01)
*G01N 33/553*   (2006.01)

(52) U.S. Cl.
CPC . *G01N 33/54393* (2013.01); *G01N 33/54306* (2013.01); *G01N 33/553* (2013.01); *G01N 33/554* (2013.01)

(58) Field of Classification Search
None
See application file for complete search history.

(56) References Cited

U.S. PATENT DOCUMENTS

| | | |
|---|---|---|
| 5,143,854 A | 9/1992 | Pirrung et al. |
| 5,424,186 A | 6/1995 | Fodor et al. |
| 5,744,305 A | 4/1998 | Fodor et al. |
| 2007/0243633 A1* | 10/2007 | Hakamata ............ G01N 33/545 436/518 |
| 2008/0130003 A1* | 6/2008 | Kuroda ................ G01N 21/554 356/445 |
| 2008/0227218 A1* | 9/2008 | Okano ................... B82Y 15/00 436/501 |
| 2011/0171629 A1* | 7/2011 | Swager ................. B82Y 15/00 435/5 |
| 2012/0064527 A1* | 3/2012 | Maekawa ............ C12Q 1/6837 435/6.11 |

* cited by examiner

*Primary Examiner* — Ann Y Lam
(74) *Attorney, Agent, or Firm* — Novick, Kim & Lee, PLLC; Jae Youn Kim

(57) ABSTRACT

Provided are molecule immobilization patterns and a method for forming the same, thereby reducing noise that may occur while analyzing a signal, being stable even at room temperature, and improving orientation of immobilized materials.

15 Claims, 3 Drawing Sheets

MOLECULE IMMOBILIZATION PATTERNS AND METHOD FOR FORMING THE SAME

CROSS-REFERENCE TO RELATED APPLICATIONS

This application claims priority under 35 U.S.C. § 119 to Korean Patent Application No. 10-2015-0103881, filed on Jul. 22, 2015, in the Korean Intellectual Property Office, the disclosure of which is incorporated herein by reference in its entirety.

TECHNICAL FIELD

The following disclosure relates to molecule immobilization patterns and a method for forming the same.

BACKGROUND

The immobilization of a specific molecule refers to formation of patterns of the specific molecule at a high density on a predetermined region of a substrate. For example, a nucleic acid or protein is capable of being immobilized with a certain shape and at a certain position on a glass or a plastic substrate. The molecule immobilization pattern is usable to perform various biological, chemical or biochemical tests or sensing. In formation of a nucleic acid molecule immobilization pattern, the predetermined region to which a target nucleic acid is immobilized is arranged at a high density on the substrate. In a microarray as a commercially available example, hybridization is generated by adding the target nucleic acid and a probe nucleic acid labeled with a detectable label (for example, fluorescent substance (fluorophore)) having complementary sequences. Then, non-hybridized target material and non-hybridized probe materials are removed by washing. Next, light amount of the fluorescent material in the hybridized material is irradiated, and fluorescence light emitting therefrom is measured by a detection system of a scanning system.

In the immobilization process of the probe materials on the surface of the substrate, a large amount of remaining probe materials are physically adsorbed onto a region other than the molecular immobilization region of the solid surface, in the process of washing the remaining probe materials which are not chemically bound, and accordingly, a noise signal may occur. Further, regardless of the bond between the target material and the probe materials on the surface of the substrate, other noise signals may also frequently occur due to other reasons at regions other than the molecule immobilization region.

Therefore, in a mechanical measurement type sensor, an electrical measurement type sensor, and the like, as well as an optical measurement type sensor, a method for forming molecule immobilization patterns capable of excluding or reducing the noise signals in order to perform an accurate sample analysis reaction has been required.

SUMMARY

An embodiment of the present invention is directed to providing a substrate for molecule immobilization including: a substrate for molecule immobilization including: a molecule immobilization region including a gold (Au)-aluminum (Al) alloy layer or a gold (Au)-silver (Ag) alloy layer formed on the substrate; and a background region which is a surface of the substrate other than the molecule immobilization region, wherein the molecule immobilization region includes gold (Au) exposed on a surface thereof.

Another embodiment of the present invention is directed to providing a method of immobilizing a molecule including: forming a molecule immobilization region to which a gold (Au) layer is deposited (or patterned) by forming the gold (Au) layer at a divided region on a surface of a substrate; forming a molecule immobilization region in which the gold (Au) layer and an aluminum (Al) layer or the gold (Au) layer and a silver (Ag) layer are deposited by forming the aluminum (Al) layer or the silver (Ag) layer on a surface of the molecule immobilization region, and forming a background region which is the surface of the substrate other than the molecule immobilization region; immobilizing a blocking agent onto the background region by contacting the blocking agent on the surface of the substrate; forming a molecule immobilization region in which a gold (Au)-aluminum (Al) alloy layer or a gold (Au)-silver (Ag) alloy layer is deposited by heating the substrate to convert the gold (Au) layer and the aluminum (Al) layer or the gold (Au) layer and the silver (Ag) layer into the gold (Au)-aluminum (Al) alloy layer or the gold (Au)-silver (Ag) alloy layer; and immobilizing the molecule onto the molecule immobilization region.

In one general aspect, a substrate for molecule immobilization includes: a molecule immobilization region including a gold (Au)-aluminum (Al) alloy layer or a gold (Au)-silver (Ag) alloy layer formed on the substrate; and a background region which is a surface of the substrate other than the molecule immobilization region, wherein the molecule immobilization region includes gold (Au) exposed on a surface thereof.

In the present specification, a term "molecule immobilization patterns" or "molecule immobilization region" may mean a divided region on a substrate onto which immobilization compounds or probe materials capable of being bound to a target material are immobilized, collection element thereof, or a region having a predetermined shape, position, or arrangement. The predetermined shape may be general shapes such as circle, rhombus, square, rectangle, star, and the like. The divided region on the substrate may be, for example, spot. The molecule immobilization region or the background region may include a plurality of regions, respectively. The background region may mean the divided region on the substrate other than the molecule immobilization region.

For example, the substrate may be a material selected from the group consisting of silicon, glass, quartz, metal, plastic, ceramic, graphene, and nanowire. Specifically, the substrate may be selected from the group consisting of silicon, glass, polystyrene, polymethyl acrylate, polycarbonate, and ceramic. The substrate may include a naturally or artificially formed oxide film. For example, when the substrate is made of silicon, the substrate may be treated with $SiO_2$ which is an oxide film. The oxide film may be substituted with other organic material films or inorganic material films. For example, the oxide film may be silicon nitride.

Formation of the oxide film on the substrate may be performed by methods known in the art. For example, the oxide film may be formed by depositing an oxide on the substrate by liquid phase deposition, evaporation, and sputtering. The substrate may have a bead shape or a spherical shape as well as a plane (plate) shape.

In addition, a molecule may be immobilized onto the surface of the substrate. The molecule may be immobilization compounds or probe materials capable of being bound to a target material. The immobilization compound may mean a material capable of being bound to the target material, or may mean a linker for immobilizing the probe materials onto the surface of the substrate. The immobilization compound may be biotin, avidin, streptavidin, carbohydrate, poly-L-lysine, a compound having a thiol group, a compound having an amine group, a compound having an alcohol group, a compound having a carboxyl group, a compound having an amino group, a compound having a sulfonic group, a compound having an aldehyde group, a compound having a carbonyl group, a compound having a succinimide group, a compound having a maleimide group, a compound having an epoxy group, or a compound having an isothiocyanate group, or combinations thereof. Examples of the compound having an amino group may include 3-aminopropyltrimethoxysilane, N-(2-amino-ethyl)-3-aminopropyltrimethoxysilane (EDA), trimethoxysilylpropyl diethylene triamine (DETA), 3-(2-amino-ethyl-amino-propyl) trimethoxysilane, and 3-aminopropyltriethoxysilane, and examples of the compound having the aldehyde group may include glutaraldehyde. Examples of the compound having a thiol group may include 4-mercaptopropyltrimethoxysilane (MPTS). In addition, examples of the compound having an epoxy group may include 3-glycidoxypropyl trimethoxysilane, and examples of the compound having an isothiocyanate group may include 4-phenylene diisothiocyanate (PDITC), and examples of the compound having a succinimide group and a maleimide group may include disuccinimidyl carbonate (DSC) or succinimidyl 4-maleimidophenyl butyrate (SMPB).

The probe material may mean a material capable of being bound to the target material. The probe material may be a material including one biomaterial monomer or a plurality of biomaterial monomers. The biomaterial may include DNA, RNA, nucleotide, nucleoside, protein, polypeptide, peptide, amino acid, carbohydrate, enzyme, antibody, antigen, receptor, virus, substrate, ligand, or membrane, and combinations thereof. Therefore, the probe materials may be immobilized onto the substrate for molecule immobilization according to an exemplary embodiment, the probe materials being selected from the group consisting of DNA, RNA, nucleotide, nucleoside, protein, polypeptide, peptide, amino acid, carbohydrate, enzyme, antibody, antigen, receptor, virus, substrate, ligand, or membrane, and combinations thereof. The monomer of the biomaterial may be nucleosides, nucleotides, amino acids, or peptides depending on kinds of the probe materials bound to the surface. The nucleoside and the nucleotide may include methylated purine or pyrimidine, acylated purine or pyrimidine, as well as purine and pyrimidine base. In addition, the nucleoside and the nucleotide may include modified sugar in which at least one hydroxyl group is substituted with a halogen atom or an aliphatic group or functional groups such as ether, amine, and the like, are bound, as well as ribose and deoxyribose sugar. The amino acid may include L-, D-amino acids found in nature, and non chiral amino acid, modified amino acid, or amino acid analog, but the amino acid of the present invention is not limited thereto. The peptide may include a compound produced by an amide bond between a carboxyl group of an amino acid and an amino group of the other amino acid.

The probe materials may be immobilized onto the substrate directly or by a linker (for example, the immobilization compound). The immobilization may be achieved by using a hydrophobic surface, a hydrophilic surface, an ion exchange surface, a metal binding surface, and the like. The molecule immobilization region is a portion including at least one probe material, and the probe materials may be immobilized onto the surface of the molecule immobilization region according to an exemplary embodiment. Depending on purpose of use according to an exemplary embodiment, the molecule immobilization region may include the probe materials which are the same as each other and/or different from each other.

The target material may include all biomaterials to be detected by using the molecule immobilization patterns. The biomaterial may include enzyme, protein, nucleic acid, sugar, virus, an antibody, microorganism, animal and plant cells and organs, nerve cells, cell organelles, DNA, or RNA. DNA may include cDNA, genomic DNA, oligonucleotide, RNA may include genomic RNA, mRNA, oligonucleotide, and examples of protein may include an antibody, an antigen, an enzyme, peptide, and the like. The biomaterial may be derived from organisms, and may include materials to be synthesized or semi-synthesized. Detecting the target material may be performed by various methods widely known to a person skilled in the art. The method may include a method using optical means. In the method using the optical means, for example, a fluorescent material may be used. The fluorescent material may be, for example, selected from the group consisting of Rhodamine 200, Calcium Green, Cyanine 2, Cyanine 3, Cyanine 5, Magnesium Green, Tetramethylrhodamine, and Fluorescein. For example, the presence and the amount of the target material may be determined by adding a sample including the target material to which the fluorescent material is bound to the substrate onto which the probe materials are immobilized, removing the target materials to which the probe materials are not bound, and confirming a signal generated from the fluorescent material bound to the target material bound to the probe material by an optical method.

The method for immobilizing the molecule onto the substrate has been widely known to a person skilled in the art. For example, the method may include activating a predefined region of the substrate and contacting the substrate with a solution including a preselected biomaterial monomer. The predefined region may be activated by light source, and other regions may be inactivated since the other regions are blocked from the light source by light mask. In addition, selectively, materials having functional groups capable of being bound to the biomaterial (immobilization compounds) may be treated on the substrate. As described above, in the forming of the molecule immobilization region by immobilizing the biomaterial such as the probe material on the substrate, adsorption, physical or chemical interaction between the substrate and the materials to be immobilized may occur, and accordingly, formation of the molecule immobilization patterns may be supported, promoted or catalyzed. For example, when the probe immobilization compound is avidin, the probe may be activated with biotin. In addition, when the probe immobilization compound has an amino group such as aminosilane, the probe may form an ester bond with a succinimide group, a maleimide group, and the like, and due to coupling reaction between the ester bond and the amino group, the probe may be immobilized. Further, for example, protein may be immobilized on the substrate using carboxymethyl-dextran. In addition, for example, the surface of the substrate may be pre-treated with chemical materials or may be bound to a number of unspecified proteins, using polylysine or calixcrown, In addition, linkers for immobilizing the antibody, virus or cell on the substrate also have been widely known.

The molecule immobilization region may include a gold (Au)-aluminum (Al) alloy layer or a gold (Au)-silver (Ag) alloy layer. In forming the alloy layer, the gold layer may be diffused into the aluminum layer or the silver layer to form the alloy layer. Accordingly, in the molecule immobilization patterns according to an exemplary embodiment, chemical properties on the surface of the molecule immobilization region may be changed. The alloy may be obtained by adding at least one element to a metal being different from the element, and may have metal properties. The gold (Au)-aluminum (Al) alloy layer may include $Al_2Au_5$, $AlAu_4$, or $Al_2Au_5$ and $AlAu_4$. In addition, the gold-aluminum alloy layer or the gold-silver alloy layer may have a thickness of 20 nm to 2 µm. Properties of the gold-aluminum alloy are described in *Scripta* Materialia 56 (2007) 549-552 by C. Xu et al., or in *Scripta* Materialia 56 (2007) 549-552 by Xu et al. Properties of the gold-silver alloy are described in Chem. Mater., 2011, 23 (18), pp 4098-4101 by Liu et al., or in Surf. Interface Anal. 28, 258-263 (1999) by Cao et al. These documents are entirely incorporated herein by reference. In addition, the molecule immobilization region may be patterned on the substrate. The patterned molecule immobilization region may have general shapes such as circle, rhombus, square, rectangle, star, and the like as described above. The plurality of molecule immobilization regions may be formed on the surface. Each molecule immobilization region may have a dimension of 0.1 µm to 1000 µm, and a distance between the regions may be 0.1 µm to 1000 µm. For example, the region may have a density of $1000/cm^2$ or more, or $10^4/cm^2$ or more, or $10^5/cm^2$ or more, or $10^6/cm^2$ or more.

Further, the immobilization compound (for example, thiol group) or the probe material immobilized to the molecule immobilization region may have a predetermined orientation in the molecule immobilization region.

A blocking agent may be immobilized onto the background region which is the surface of the substrate other than the molecule immobilization region. For example, the background region which is the surface of the substrate other than the molecule immobilization region may include a blocking layer including the blocking agent. The blocking agent may include a material capable of inhibiting non-specific binding between the substrate and the probe materials or the immobilization compounds, and may have activity of inhibiting physical change, that is, activity of inhibiting the non-specific binding even at a heating temperature for forming the alloy. The blocking agent may be a material including alkene thiol molecules, or may be a material blocking bio-fouling. For example, example of the blocking agent may include 6-mercapto-1-hexanol (MCH), 11-mercaptoundecanoic acid (MUA), 1-hexadecane thiol, bovine serum albumin (BSA), casein, fetal bovine serum (FBS), dextran, polyethylene glycol (PEG), polyethylene oxide (PEO), or combinations thereof.

In an exemplary embodiment, the molecule, for example, the immobilization compound or the probe material may not be substantially immobilized onto the background region other than the molecule immobilization region. The expression: "the immobilization compound or the probe material is not substantially immobilized" may include a case in which the immobilization compound or the probe material is hardly or not immobilized at all onto the background region other than the molecule immobilization region by the blocking agent coated on the surface of the substrate. Further, since the blocking agent is not substantially coated onto the molecule immobilization region, the immobilization compounds or the probe materials may be immobilized onto the molecule immobilization region. Otherwise, the opposite case thereof may occur. The expression: "the blocking agent is not substantially coated" may include a case in which the blocking agent is hardly or absolutely not immobilized onto the molecule immobilization region by the gold-aluminum alloy, or the gold-silver alloy included in the molecule immobilization region. For example, the blocking agent may generally serve to inhibit the non-specific binding between the probe materials causing noise and the substrate in the background region other than the molecule immobilization region, but the probe materials may not be immobilized even to the molecule immobilization region in which gold is deposited, due to the use of the blocking agent. However, by constituting the molecule immobilization region selectively including the gold-aluminum alloy or the gold-silver alloy by heat or other physical methods, the blocking agent is not substantially coated onto the molecule immobilization region due to aluminum or silver included in the alloy, such that property of the gold may be exhibited after the treatment. Therefore, in the molecule immobilization patterns according to an exemplary embodiment, the non-specific binding of the immobilization compounds or the probe materials may be inhibited by the blocking agent at the region other than the molecule immobilization region, and the immobilization compounds or the probe materials may be immobilized to the molecule immobilization region since the blocking agent capable of inhibiting the non-specific binding is not coated onto the molecule immobilization region. Further, the molecule immobilization region in which gold is deposited is easily contaminated at room temperature by property of gold, but the molecule immobilization region according to an exemplary embodiment of the present invention is not contaminated at room temperature.

Another embodiment of the present invention is directed to providing a biochip including a substrate for molecule immobilization, the substrate including: a molecule immobilization region including a gold (Au)-aluminum (Al) alloy layer or a gold (Au)-silver (Ag) alloy layer formed on the substrate; and a background region which is a surface of the substrate other than the molecule immobilization region, wherein the molecule immobilization region includes gold (Au) exposed on a surface thereof.

In the present specification, a term "biochip" may be used as known in the art. That is, it means that the specific material, for example, the probe material bound to the target material may be immobilized to the divided region on the substrate. The biochip may include a DNA chip, a protein chip, a cell chip, array (for example, microarray) or a biosensor. The DNA chip may mean a chip in which DNA probe is immobilized, the protein chip may mean a chip using protein such as an enzyme or antibody/antigen, the cell chip may mean a chip using animal/plant cell, and the biosensor may mean a sensor in which biological materials are combined with the existing physical, chemical and optical sensor signal converter. For example, in the sensor including the substrate for molecule immobilization, the sensor may include a mechanical measurement type sensor or an electrical measurement type sensor, and the like, as well as an optical measurement type sensor. The mechanical measurement type sensor may include a cantilever sensor, a quartz crystal monitor (QCM) sensor, or a suspended microchannel resonator (SMR) sensor, and the electrical measurement type sensor may include a field effect transistor (FET) sensor or a radio frequency (RF) sensor. The molecule immobilization patterns according to an exemplary embodiment of the present invention may reduce occurrence of noise signal even in the mechanical measurement type sensor or the electrical measurement type sensor as described above as well as the optical measurement type sensor, thereby effectively amplifying signal.

Another embodiment of the present invention is directed to providing a method of immobilizing a molecule including: forming a molecule immobilization region to which a gold (Au) layer is deposited (or patterned) by forming the gold (Au) layer at a divided region on a surface of a substrate; forming a molecule immobilization region in which the gold (Au) layer and an aluminum (Al) layer or the gold (Au) layer and a silver (Ag) layer are deposited by forming the aluminum (Al) layer or the silver (Ag) layer on a surface of the molecule immobilization region, and a background region which is the surface of the substrate other than the molecule immobilization region; immobilizing a blocking agent onto the background region by contacting the blocking agent on the surface of the substrate; forming a molecule immobilization regions in which a gold (Au)-aluminum (Al) alloy layer or a gold (Au)-silver (Ag) alloy layer is deposited by heating the substrate to convert the gold (Au) layer and the aluminum (Al) layer or the gold (Au) layer and the silver (Ag) layer into the gold (Au)-aluminum (Al) alloy layer or the gold (Au)-silver (Ag) alloy layer; and immobilizing the molecule onto the molecule immobilization region.

The substrate, the alloy layer, and the molecule immobilization region are described as above.

In the forming of the molecule immobilization region to which the gold (Au) layer is deposited (or patterned), or in the forming of the molecule immobilization region in which the gold (Au) layer and the aluminum (Al) layer or the gold (Au) layer and the silver (Ag) layer are deposited, the gold (Au) layer, the aluminum (Al) layer, or the silver (Ag) layer may have a thickness of 0.01 nm to 1000 μm. The method for forming the gold layer, the aluminum layer, or the silver layer may be any method known to a person skilled in the art. For example, the method may be any one selected from the group consisting of a spin coating method, a dip coating method, a dropping method, a gravure printing method, a screen printing method, an anastatic printing method, a die coating method, a curtain coating method, an inkjet method, a spray coating method, a sputtering method, and a vacuum vapor deposition method. For example, the forming of the molecule immobilization region to which the gold (Au) layer is deposited (or patterned) may include forming the molecule immobilization region to which the gold (Au) layer is deposited (or patterned) at the divided region on the substrate by forming the gold (Au) layer through a mask on the substrate, or the forming of the molecule immobilization region in which the gold (Au) layer and the aluminum (Al) layer or the gold (Au) layer and the silver (Ag) layer are deposited may include forming the molecule immobilization region in which the gold (Au) layer and the aluminum (Al) layer or the gold (Au) layer and the silver (Ag) layer are deposited by forming the aluminum (Al) layer or the silver (Ag) layer through a mask on the surface of the molecule immobilization region in which the gold (Au) layer is deposited. For example, the gold layer, the aluminum layer, or the silver layer may be deposited under a vacuum state. For example, the vacuum state may mean a pressure condition of 1 Torr or less. Further, for example, the pressure condition may mean 10-7 Torr or more, 10-6 Torr or 10-5 Torr or more. In addition, for example, the forming of the molecule immobilization region to which the gold (Au) layer is deposited (or patterned), and the forming the molecule immobilization region in which the gold (Au) layer and the aluminum (Al) layer or the gold (Au) layer and the silver (Ag) layer are deposited may include: forming the gold (Au) layer on the substrate; forming the aluminum layer or the silver layer on the gold (Au) layer; coating a photoresist on the substrate on which the gold (Au) layer and the aluminum (Al) layer or the gold (Au) layer and the silver (Ag) layer are formed; exposing the coated photoresist layer through a mask; developing the exposed photoresist layer and forming the divided region on the substrate which is protected or not protected by the photoresist layer; etching the gold (Au) layer and the aluminum (Al) layer of the divided region on the substrate which is not protected by the photoresist layer so that the divided region on the substrate which is not protected by the photoresist layer is formed to be the background region, and the divided region on the substrate which is protected by the photoresist layer is formed to be the molecule immobilization region in which the gold (Au) layer and the aluminum (Al) layer or the gold (Au) layer and the silver (Ag) layer are deposited; and removing the photoresist layer coated on the molecule immobilization region in which the gold (Au) layer and the aluminum (Al) layer or the gold (Au) layer and the silver (Ag) layer are deposited. The developing of the photoresist layer may be performed by treating the exposed photoresist layer with a development solution, and washing as needed. The development solution may be selected according to the photoresist. After development, the region which is not protected by the photoresist layer may be etched to form a reference point marker. For example, the etching may be performed by wet etching or dry etching. The removing of the photoresist layer may be performed by methods known in the art. For example, the photoresist layer may be removed by organic solvents dissolving the photoresist, for example, acetone.

The immobilizing of the blocking agent onto the background region by contacting the blocking agent on the surface of the substrate may include immersing the substrate in a solution including the blocking agent or dropping the solution on the substrate. The treatment with the blocking agent may be performed for at least 15 minutes, about 15 minutes to about 72 hours, about 30 minutes to about 60 hours, or about 30 minutes to about 48 hours. The solution including the blocking agent may have a concentration of at least 0.5 mM, for example, about 0.5 mM to about 20 mM, about 0.5 mM to about 15 mM, about 1.0 mM to about 15 mM, about 2.0 mM to about 10 mM. After treating the blocking agent, remaining blocking agent may be washed by washing the substrate with aqueous solution (for example, distilled water).

In the heating of the substrate, the gold (Au) layer may be diffused into the aluminum layer, or the silver layer by the heating (heat treatment) to form the gold-aluminum alloy layer or the gold-silver alloy layer. The forming of the alloy layer may be confirmed by observing change in color of the surface of aluminum or silver deposited on the gold in a sequence of white, red, and gold. The heating may be performed by selecting appropriate temperature range and appropriate time range by a person skilled in the art. For example, the heating temperature may be about 40° C. to about 500° C., about 60° C. to about 450° C., about 100° C. to about 350° C., about 150° C. to about 280° C., or about 180° C. to about 250° C. In addition, the heating time may be about 10 minutes to about 24 hours, about 30 minutes to about 20 hours, about 1 hour to about 16 hours, about 4 hours to about 16 hours, or about 8 hours to about 12 hours.

The immobilizing of the molecule onto the molecule immobilization region may be performed after the forming of the molecule immobilization region in which the gold (Au)-aluminum (Al) alloy layer or the gold (Au)-silver (Ag) alloy layer is deposited. The molecule is the same as described above. The immobilizing of the molecule may include contacting a molecule to be immobilized on the substrate. The molecule, for example, the probe material may include a thiol group to be immobilized to the gold exposed onto the surface of the molecule immobilization region directly or by a linker. For example, the method for immobilization may include a method using photolithography, and a method using spotting. The method using photolithography may be performed by repeating a step of exposing a predetermined region on a surface of a substrate to which a monomer protected with a removable group is deposited to energy source, thereby removing the protected group, and a step of coupling the monomer protected with the removable group. In this case, each probe monomer immobilized onto the substrate may be synthesized in the extension manner for one by one. Further, according to the method using spotting, pre-synthesized probe may be immobilized to a predetermined position on the substrate. For example, the immobilization method is described in U.S. Pat. Nos. 5,744,305, 5,143,854 and 5,424,186.

In an exemplary embodiment, the molecule, for example, the immobilization compound or the probe material may not be substantially immobilized onto the background region other than the molecule immobilization region. Further, since the molecule immobilization region is not substantially coated with the blocking agent, the immobilization compounds or the probe materials may be immobilized onto the molecule immobilization region. By forming the molecule immobilization region including the gold-aluminum alloy or the gold-silver alloy, the blocking agent is not substantially coated onto the molecule immobilization region due to aluminum or silver included in the alloy, such that property of the gold may be exhibited after the treatment. Therefore, according to an exemplary embodiment of the present invention, the non-specific binding of the immobilization compounds or the probe materials may be inhibited by the blocking agent at the background region other than the molecule immobilization region, and the blocking agent capable of inhibiting the non-specific binding is not coated onto the molecule immobilization region, such that the immobilization compounds or the probe materials may be immobilized onto the molecule immobilization region.

DETAILED DESCRIPTION OF EMBODIMENTS

Figure 1A:
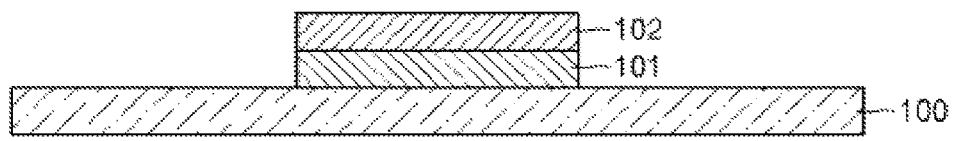
FIGS. 1A-1D are views illustrating a method for forming molecule immobilization patterns according to an exemplary embodiment of the present invention.
Figure 1B:
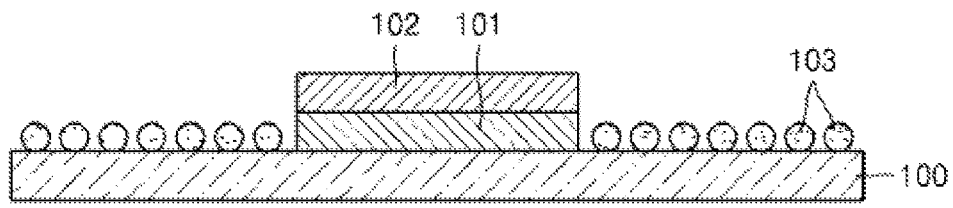
Figure 1C:
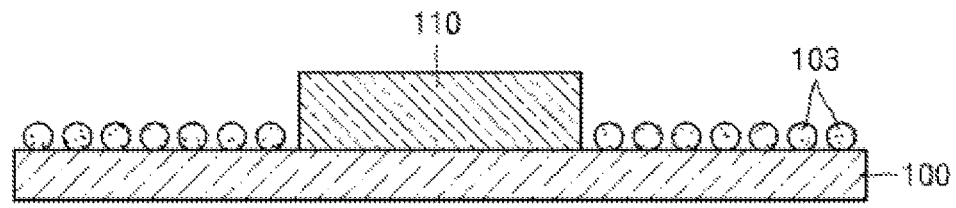
Figure 1D:
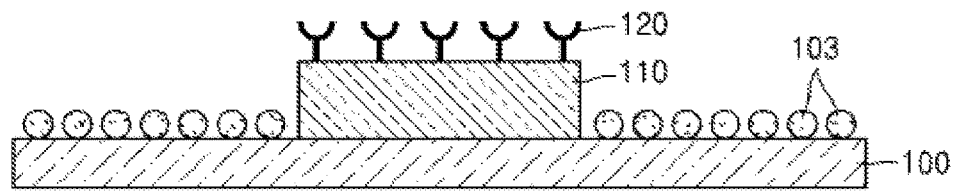

Hereinafter, examples of the present invention will be described in detail with reference to the accompanying drawings. However, the accompanying drawings and Examples are provided to illustrate the present invention by way of example, and accordingly, the scope of the present invention is not limited to the accompanying drawings and Examples.

FIGS. 1A-1D are views illustrating a method for forming molecule immobilization patterns according to an exemplary embodiment of the present invention. Referring to FIGS. 1A-1D, there is a method of immobilizing a molecule including: forming a molecule immobilization region 110 to which a gold (Au) layer 101 is deposited (or patterned), by forming the gold (Au) layer at a divided region on a surface of a substrate 100; forming a molecule immobilization region 110 in which the gold (Au) layer 101 and an aluminum (Al) layer 102 or the gold (Au) layer 101 and a silver (Ag) layer 102 are deposited, by forming the aluminum (Al) layer 102 or the silver (Ag) layer 102 on a surface of the molecule immobilization region 110, and forming a background region 103 which is the surface of the substrate 100 other than the molecule immobilization region 110; immobilizing a blocking agent 103 onto the background region by contacting the blocking agent 103 on the surface of the substrate 100; forming a molecule immobilization region 110 in which a gold (Au)-aluminum (Al) alloy layer or a gold (Au)-silver (Ag) alloy layer is deposited, by heating the substrate 100 to convert the gold (Au) layer 101 and the aluminum (Al) layer 102 or the gold (Au) layer 101 and the silver (Ag) layer 102 into the gold (Au)-aluminum (Al) alloy layer or the gold (Au)-silver (Ag) alloy layer; and immobilizing a molecule 120 onto the molecule immobilization region 110.

In the forming of the molecule immobilization region 110 to which a gold (Au) layer 101 is deposited (or patterned), or in the forming of the molecule immobilization region 110 in which a gold (Au) layer 101 and an aluminum (Al) layer 102 or a gold (Au) layer 101 and a silver (Ag) layer 102 are deposited, the gold (Au) layer 101, the aluminum (Al) layer 102, or the silver (Ag) layer 102 may have a thickness of 0.01 nm to 1000 µm. A method for forming the gold layer 101, the aluminum layer 102, or the silver layer 102 may be any method known to a person skilled in the art. For example, the method may be any one selected from the group consisting of a spin coating method, a dip coating method, a dropping method, a gravure printing method, a screen printing method, an anastatic printing method, a die coating method, a curtain coating method, an inkjet method, a spray coating method, a sputtering method, and a vacuum vapor deposition method. The immobilizing of the blocking agent 103 onto the background region by contacting the blocking agent 103 on the surface of the substrate 100 may include immersing the substrate 100 in a solution including the blocking agent 103 or dropping the solution on the substrate 100. The treatment with the blocking agent may be performed for at least 15 minutes, about 15 minutes to about 72 hours, about 30 minutes to about 60 hours, or about 30 minutes to about 48 hours. The solution including the blocking agent may have a concentration of at least 0.5 mM, for example, about 0.5 mM to about 20 mM, about 0.5 mM to about 15 mM, about 1.0 mM to about 15 mM, about 2.0 mM to about 10 mM. After the treatment with the blocking agent 103, remaining blocking agent may be washed by washing the substrate 100 with aqueous solution (for example, distilled water). In the heating of the substrate 100, the gold (Au) layer 101 may be diffused into the aluminum layer 102, or the silver layer 102 by the heating (heat treatment) to form the gold-aluminum alloy layer or the gold-silver alloy layer. The forming of the alloy layer may be confirmed by observing change in color of the surface of aluminum or silver deposited on the gold in a sequence of white, red, and gold. The heating may be performed by selecting appropriate temperature range and appropriate time range by a person skilled in the art. For example, the heating temperature may be about 40° C. to about 500° C., about 60° C. to about 450° C., about 100° C. to about 350° C., about 150° C. to about 280° C., or about 180° C. to about 250° C. In addition, the heating time may be about 10 minutes to about 24 hours, about 30 minutes to about 20 hours, about 1 hour to about 16 hours, about 4 hours to about 16 hours, or about 8 hours to about 12 hours. The immobilizing of the molecule 120 onto the molecule immobilization region 110 may be performed after the forming of the molecule immobilization region 110 in which a gold (Au)-aluminum (Al) alloy layer or a gold (Au)-silver (Ag) alloy layer is deposited. The molecule 120 is the same as described above. The immobilizing of the molecule 120 may include contacting the molecule 120 to be immobilized on the substrate.

Figure 2:
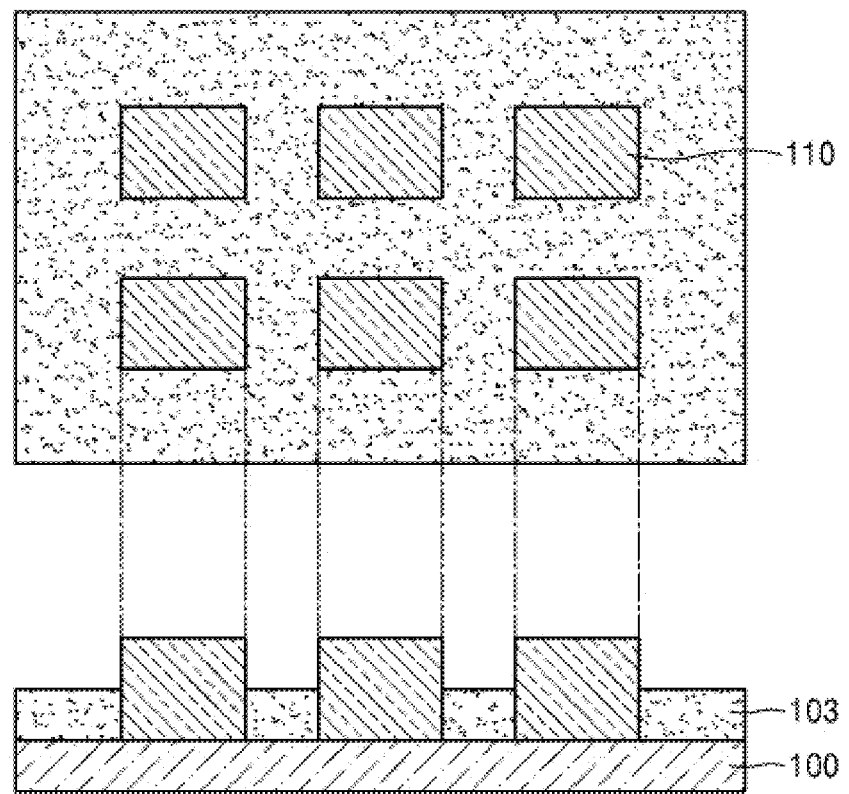
FIG. 2 is a view illustrating one example of the molecule immobilization patterns according to an exemplary embodiment of the present invention.

FIG. 2 is a view illustrating one example of the molecule immobilization patterns including the substrate 100 and the gold (Au)-aluminum (Al) alloy layer formed on the substrate 100. The molecule may be immobilized onto the molecule immobilization region 110. The molecule immobilization region 110 may be formed in plural or with various arrangements on the surface of the substrate 100. The molecule immobilization region 110 may include various kinds of probe materials or immobilization compounds capable of being bound to a target material. The target material may be a biomaterial to be detected. For example, when the target material to be detected is a single stranded DNA having a specific sequence, the probe material is complementary single stranded DNA, and when the target material to be detected is an antigen having a specific three-dimensional structure, an antibody material is an antibody capable of being structurally bound to the antigen. The molecule immobilization region 110 may include the gold (Au)-aluminum (Al) alloy layer or the gold (Au)-silver (Ag) alloy layer. Properties of the gold-aluminum alloy are described in *Scripta* Materialia 56 (2007) 549-552 by C. Xu et al. Properties of the gold-silver alloy are described in Chem. Mater., 2011, 23 (18), pp 4098-4101 by Liu et al., or in Surf. Interface Anal. 28, 258-263 (1999) by Cao et al. These documents are entirely incorporated herein by reference. In addition, the molecule immobilization region may be patterned on the substrate. The patterned molecule immobilization region may have general shapes such as circle, rhombus, square, rectangle, star, and the like as described above. The plurality of molecule immobilization regions may be formed on the surface. Each molecule immobilization region may have a dimension of 0.1 μm to 1000 μm, and a distance between the regions may be 0.1 μm to 1000 μm. For example, the region may have a density of $1000/cm^2$ or more, or $10^4/cm^2$ or more, or $10^5/cm^2$ or more, or $10^6/cm^2$ or more. In addition, the background region which is a region other than the molecule immobilization region formed on the substrate 100 may be coated with the blocking agent.

The molecule, for example, the immobilization compounds or the probe materials may not be substantially immobilized onto the background region other than the molecule immobilization region. Further, since the blocking agent is not substantially coated onto the molecule immobilization region, the immobilization compounds or the probe materials may be immobilized onto the molecule immobilization region. Otherwise, the opposite case thereof may occur. For example, the blocking agent may generally serve to inhibit non-specific binding between the probe materials causing noise and the substrate in the background region other than the molecule immobilization region, but the probe materials may not be immobilized even to the molecule immobilization region in which gold is deposited, due to the use of the blocking agent. However, by constituting the molecule immobilization region selectively including the gold-aluminum alloy or the gold-silver alloy by heat or other physical methods, the blocking agent is not substantially coated onto the molecule immobilization region due to aluminum or silver included in the alloy, such that property of the gold may be exhibited after the treatment. Therefore, in the molecule immobilization patterns according to an exemplary embodiment, the non-specific binding of the immobilization compounds or the probe materials may be inhibited by the blocking agent at the background region other than the molecule immobilization region, and the immobilization compounds or the probe materials may be immobilized to the molecule immobilization region since the blocking agent capable of inhibiting the non-specific binding is not coated onto the molecule immobilization region. Further, the molecule immobilization region in which gold is deposited is easily contaminated at room temperature by property of gold, but the molecule immobilization region according to an exemplary embodiment of the present invention is not contaminated at room temperature.

EXAMPLE

Formation of Molecule Immobilization Patterns and Detection of Target Material Using the Same 1. Formation of Molecule Immobilization Patterns The molecule immobilization patterns were formed as follows.

First, a silicon substrate having a nitride surface was used for a substrate. Sputtering was used to form a gold (Au) layer and an aluminum (Al) layer on the substrate. Specifically, a stencil mask was put on the substrate, and the gold layer was deposited at a thickness of 50 nm at a temperature of 25° C. under a vacuum state having pressure of 1 Torr or less. Next, the aluminum layer was deposited at a thickness of 100 nm on the gold layer by the same method as the gold layer. Then, the substrate was immersed in DMF solution including 6-mercapto-1-hexanol (MCH) having a concentration of 10 mM which is the blocking agent, followed by stirring for 12 hours or more. Then, the substrate was removed from the solution, and washed with distilled water. The washed substrate was put at a temperature of 120° C. for heat treatment. The heat treatment was performed for 5 minutes, 10 minutes, 20 minutes, and 30 minutes, respectively, to form the molecule immobilization patterns.

2. Detection of Target Material

In order to confirm detectability of a target material of the formed molecule immobilized patterns, DNA aptamer (5'-AAA-Cy5-3') was immobilized onto the substrate.

In the immobilization, specifically, DNA aptamer (5'-HS-C6-AAA-Cy5-3') having thiol attached thereto was used as a test group, and DNA aptamer (5'-AAA-Cy5-3') without thiol was used as a control group. A solution including each aptamer at a concentration of 1 μM was spotted on the substrate and reacted for 2 hours for immobilization. Then, remaining aptamer which was not immobilized was removed by washing the substrate with distilled water. The aptamer was detected by fluorescent images at 500 nm using fluorescent scanner (GenePix 4000B), and results thereof were illustrated in FIGS. 3 and 4, respectively.

Figure 3:
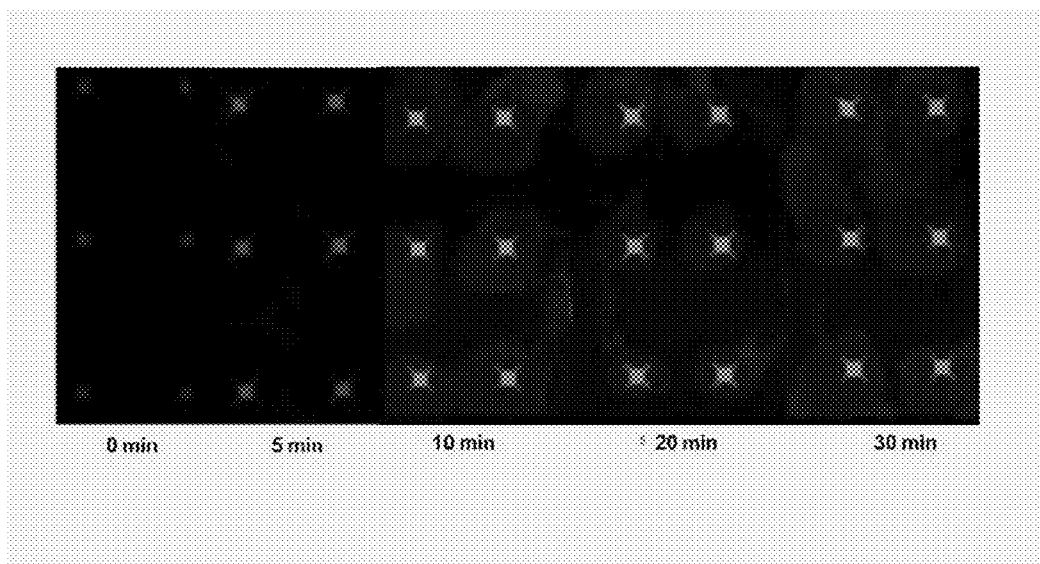
FIG. 3 is a view illustrating results obtained by detecting a target material using the molecule immobilization patterns according to an exemplary embodiment of the present invention.

FIG. 3 is a view illustrating results obtained by detecting the target material using the molecule immobilization patterns according to an exemplary embodiment of the present invention.

Figure 4:
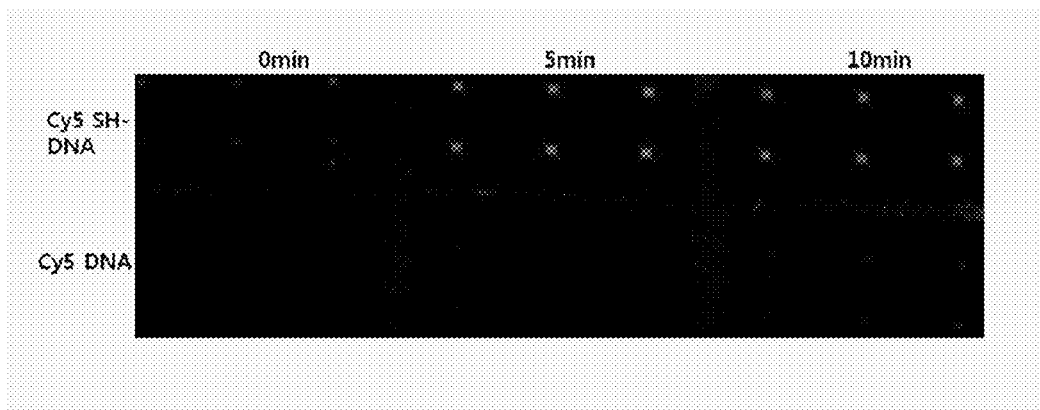
FIG. 4 is a view illustrating results obtained by detecting a target material using the molecule immobilization patterns according to an exemplary embodiment of the present invention.

FIG. 4 is a view illustrating results obtained by detecting the target material using the molecule immobilization patterns according to an exemplary embodiment of the present invention.

As illustrated in FIG. 3, it could be confirmed that the aptamer which is the target material in the molecule immobilization region in which the gold (Au)-aluminum (Al) alloy layer is formed according to an exemplary embodiment of the present invention was detected only at the molecule immobilization region, and noise hardly occurred at the background region.

In addition, as illustrated in FIG. 4, it could be confirmed that the aptamer having a thiol group attached thereto which is the target material was capable of being specifically detected at the molecule immobilization region in which the gold-aluminum alloy is formed according to the exemplary embodiment.

The present invention provides the molecule immobilization patterns and the method for forming the same, thereby reducing noise that may occur while analyzing a signal, being stable even at room temperature, and improving orientation of immobilized materials.

What is claimed is:

1. A substrate for molecule immobilization, comprising:
a molecule immobilization region including a gold (Au)-aluminum (Al) alloy layer or a gold (Au)-silver (Ag) alloy layer formed on the substrate;
a background region which is a surface of the substrate other than the molecule immobilization region; and
a blocking agent immobilized onto the background region,
wherein the molecule immobilization region includes gold (Au) exposed on a surface thereof.

2. The substrate for molecule immobilization of claim 1, wherein the gold (Au)-aluminum (Al) alloy layer includes $Al_2Au_5$, $AlAu_4$, or $Al_2Au_5$ and $AlAu_4$.

3. The substrate for molecule immobilization of claim 1, wherein the gold (Au)-aluminum (Al) alloy layer or the gold (Au)-silver (Ag) alloy layer has a thickness of 20 nm to 2 μm.

4. The substrate for molecule immobilization of claim 1, wherein the molecule immobilization region and the background region include a plurality of regions, respectively.

5. The substrate for molecule immobilization of claim 1, wherein probe materials or immobilization compounds capable of being bound to a target material are immobilized onto the surface of the molecule immobilization region.

6. The substrate for molecule immobilization of claim 1, wherein the blocking agent is 6-mercapto- 1-hexanol (MCH), 11-mercaptoundecanoic acid (MUA), 1-hexadecane thiol, bovine serum albumin (BSA), casein, fetal bovine serum (FBS), dextran, polyethylene glycol (PEG), polyethylene oxide (PEO), or combinations thereof.

7. The substrate for molecule immobilization of claim 1, wherein the substrate is selected from the group consisting of silicon, glass, quartz, metal, plastic, ceramic, graphene, and nanowire.

8. The substrate for molecule immobilization of claim 5, wherein the probe materials are DNA, RNA, nucleotide, nucleoside, protein, polypeptide, amino acid, carbohydrate, enzyme, antibody, antigen, receptor, virus, substrate, ligand, or combinations thereof.

9. The substrate for molecule immobilization of claim 5, wherein the immobilization compound is biotin, avidin, streptavidin, carbohydrate, poly-L-lysine, a compound having a thiol group, a compound having an amine group, a compound having an alcohol group, a compound having a carboxyl group, a compound having an amino group, a compound having a sulfonic group, a compound having an aldehyde group, a compound having a carbonyl group, a compound having a succinimide group, a compound having a maleimide group, a compound having an epoxy group, or a compound having an isothiocyanate group, or combinations thereof.

10. A method of immobilizing a molecule, the method comprising:
forming a molecule immobilization region, including forming a gold (Au) layer on a divided region of a surface of a substrate, and forming an aluminum (Al) layer or a silver (Ag) layer on the gold (Au) layer; and
forming a background region which is a surface of the substrate other than the molecule immobilization region;
immobilizing a blocking agent onto the background region by coating the blocking agent on the surface of the substrate other than the molecule immobilzation region;
heating the substrate to convert the gold (Au) layer and the aluminum (Al) layer or the gold (Au) layer and the silver (Ag) layer into a gold (Au)-aluminum (Al) alloy layer or a gold (Au)-silver (Ag) alloy layer, respectively; and
immobilizing the molecule onto the molecule immobilization region.

11. The method of claim 10, wherein in the forming of the molecule immobilization region to which the gold (Au) layer is patterned, or in the forming of the molecule immobilization region in which the gold (Au) layer and the aluminum (Al) layer or the gold (Au) layer and the silver (Ag) layer are deposited, the gold (Au) layer, the aluminum (Al) layer, or the silver (Ag) layer has a thickness of 0.01 nm to 1000 μm.

12. The method of claim 10, wherein the gold (Au) layer and the aluminum (Al) layer, or the gold (Au) layer and the silver (Ag) layer are formed at a thickness ratio of 1:5 to 5:1.

13. The method of claim 10, wherein
forming the gold (Au) layer is performed through a mask on the substrate, or
the forming of the aluminum (Al) layer or the silver (Ag) layer is performed through a mask on the surface of the molecule immobilization region in which the gold (Au) layer is deposited.

14. The method of claim 10, wherein the forming of the molecule immobilization region further includes:
coating a photoresist on the substrate on which the gold (Au) layer and the aluminum (Al) layer or the gold (Au) layer and the silver (Ag) layer are formed;
exposing the coated photoresist layer through a mask;
developing the exposed photoresist layer and forming the divided region on the substrate which is protected or not protected by the photoresist layer;
etching the gold (Au) layer and the aluminum (Al) layer of the divided region on the substrate which is not protected by the photoresist layer so that the divided region on the substrate which is not protected by the photoresist layer is formed to be the background region, and the divided region on the substrate which is protected by the photoresist layer is formed to be the molecule immobilization region in which the gold (Au)

layer and the aluminum (Al) layer or the gold (Au) layer and the silver (Ag) layer are deposited; and removing the photoresist layer coated on the molecule immobilization region in which the gold (Au) layer and the aluminum (Al) layer or the gold (Au) layer and the silver (Ag) layer are deposited.

15. The method of claim 10, wherein the heating is performed at a temperature of 40° C. to 500° C.

* * * * *